(12) United States Patent
Sarr et al.

(10) Patent No.: US 10,184,916 B2
(45) Date of Patent: Jan. 22, 2019

(54) SYSTEMS, METHODS, AND DEVICES FOR PROBE ASSEMBLIES FOR VARIABLE CURVATURE AND VARIABLE ANGLE CONFIGURATIONS

(71) Applicant: The Boeing Company, Chicago, IL (US)

(72) Inventors: Dennis Sarr, Seattle, WA (US); Hien Bui, Renton, WA (US); Christopher Brown, Seattle, WA (US)

(73) Assignee: The Boeing Company, Chicago, IL (US)

( * ) Notice: Subject to any disclaimer, the term of this patent is extended or adjusted under 35 U.S.C. 154(b) by 386 days.

(21) Appl. No.: 14/997,247

(22) Filed: Jan. 15, 2016

(65) Prior Publication Data

US 2017/0205378 A1     Jul. 20, 2017

(51) Int. Cl.
| | |
|---|---|
| *G01N 29/265* | (2006.01) |
| *G01N 29/24* | (2006.01) |
| *G01N 29/04* | (2006.01) |
| *G01N 29/22* | (2006.01) |

(52) U.S. Cl.
CPC ....... *G01N 29/2487* (2013.01); *G01N 29/041* (2013.01); *G01N 29/225* (2013.01); *G01N 29/265* (2013.01); *G01N 2291/0231* (2013.01); *G01N 2291/269* (2013.01)

(58) Field of Classification Search
CPC .. G01N 29/2487; G01N 29/26; G01N 29/265; G01N 29/225; G01N 29/041; G01N 29/24; G01N 29/221; G01N 2291/0231; G01N 2291/2694; G01N 2291/2638

USPC ................. 73/620, 627, 633, 634, 635, 640
See application file for complete search history.

(56) References Cited

U.S. PATENT DOCUMENTS

| | | | | |
|---|---|---|---|---|
| 2,940,305 | A | * | 6/1960 | Williams ........... G01N 29/2487 |
| | | | | 250/491.1 |
| 3,955,425 | A | * | 5/1976 | Corneau ................. B29C 47/92 |
| | | | | 73/622 |
| 4,807,476 | A | | 2/1989 | Cook et al. |
| 5,585,564 | A | | 12/1996 | Brunty et al. |
| 7,263,889 | B2 | | 9/2007 | Kennedy et al. |
| 7,484,413 | B2 | | 2/2009 | Georgeson et al. |
| 7,836,768 | B2 | | 11/2010 | Young et al. |

(Continued)

*Primary Examiner* — Manish S Shah
*Assistant Examiner* — Rose M Miller
(74) *Attorney, Agent, or Firm* — Kwan & Olynick LLP

(57) ABSTRACT

Systems, methods, and devices are disclosed for inspecting a manufacturing component. Devices include a centering device configured to modify a position of an ultrasonic probe assembly relative to a manufacturing component to bisect an angle associated with the manufacturing component. Devices may also include a surface sensing device configured to sense a curvature associated with the manufacturing component. Devices may further include a plurality of sensors configured to measure a first displacement value associated with the centering device and a second displacement value associated with the surface sensing device. The devices may include a control circuit configured to determine a position adjustment value based on at least one of the first displacement value and the second displacement value. The devices may also include an actuator configured to modify a position of an ultrasonic transducer based, at least in part, on the position adjustment value.

20 Claims, 9 Drawing Sheets

(56) References Cited

U.S. PATENT DOCUMENTS

2005/0126294 A1   6/2005  Bossi et al.
2009/0107244 A1*  4/2009  Fetzer ................. G01N 29/225
                                              73/635

* cited by examiner

SYSTEMS, METHODS, AND DEVICES FOR PROBE ASSEMBLIES FOR VARIABLE CURVATURE AND VARIABLE ANGLE CONFIGURATIONS

TECHNICAL FIELD

This disclosure generally relates to vehicles and machinery and, more specifically, to probe assemblies associated with vehicles.

BACKGROUND

Various manufacturing components, such as vehicle parts, may be utilized during a manufacturing process. Such manufacturing components may be composite structures formed from a composite of materials. The formation of such composite structures as well as various other types of manufacturing components may sometimes inadvertently include structural defects within the manufacturing components themselves. Accordingly, the manufacturing components may be scanned to assess a quality of the manufacturing components and identify any structural defects that may be included within the manufacturing components. One particular scanning technique utilizes ultrasonic energy to generate a representation or image of the inside of a particular portion of the manufacturing component. The generated representation may be used to identify defects, such as cracks and voids.

SUMMARY

Provided are one or more probe assemblies that may be used to scan parts and manufacturing components associated with one or more vehicles. Devices as disclosed herein may include a centering device configured to modify a position of an ultrasonic probe assembly relative to a manufacturing component to bisect an angle associated with the manufacturing component. Devices may also include a surface sensing device configured to sense a curvature associated with the manufacturing component. Devices may further include a plurality of sensors configured to measure a first displacement value associated with the centering device and a second displacement value associated with the surface sensing device. The devices may include a control circuit configured to determine a position adjustment value based on at least one of the first displacement value and the second displacement value. The devices may also include an actuator configured to modify a position of an ultrasonic transducer based, at least in part, on the position adjustment value.

Devices as disclosed herein may include a centering device configured to modify a position of an ultrasonic probe assembly relative to a manufacturing component to bisect an angle associated with the manufacturing component. Devices may also include a surface sensing device configured to sense a curvature associated with the manufacturing component. Devices may further include a plurality of sensors configured to measure a first displacement value associated with the centering device and a second displacement value associated with the surface sensing device. The devices may include a control circuit configured to determine a position adjustment value based on at least one of the first displacement value and the second displacement value. The devices may also include an actuator configured to modify a position of an ultrasonic transducer based, at least in part, on the position adjustment value.

In some embodiments, the centering device includes a first surface following guide, a second surface following guide, and a coupling housing coupled to the first surface following guide and the second surface following guide. The coupling housing may be biased by a first tension device. Moreover, the plurality of sensors may include a first sensor and a second sensor. In various embodiments, the first sensor is coupled to the centering device, and the second sensor is coupled to the surface sensing device. In some embodiments, the first sensor and the second sensor include differential variable reluctance transformers, and the control circuit includes a processor and a non-volatile memory.

In various embodiments, at least one of the first displacement value and second displacement value identifies a change in the angle associated with the manufacturing component or a change in a position of the ultrasonic probe assembly relative to the manufacturing component. In some embodiments, the position adjustment value identifies a positional adjustment configured to modify a position of the ultrasonic transducer to offset the change. In various embodiments, the actuator is configured to modify the position of the ultrasonic transducer to offset the change. In some embodiments, the ultrasonic transducer is configured to measure one or more structural properties of the manufacturing component. According to some embodiments, the surface sensing device includes a wheel biased by a second tension device.

Methods are also disclosed herein that may include positioning, using a centering device, an ultrasonic probe assembly relative to a manufacturing component to bisect an angle associated with the manufacturing component. The methods may also include identifying a change associated with the position of the ultrasonic probe assembly relative to the manufacturing component. The methods may further include determining, using a control circuit, a position adjustment value based on the identified change. The methods may further include modifying a position of an ultrasonic transducer based, at least in part, on the position adjustment value.

The identifying the change may include identifying, using a first sensor associated with the centering device, a first displacement value. The identifying the change may also include identifying, using a second sensor associated with a surface sensing device, a second displacement value. In some embodiments, the surface sensing device comprises a wheel biased by a tension device. Moreover, the modifying of the position of the ultrasonic transducer may be based, at least in part, on the position adjustment value, and offsets the identified change.

Also disclosed are systems that may include a robotic arm and an ultrasonic probe assembly coupled to the robotic arm. The ultrasonic probe assembly may include a centering device configured to modify a position of the ultrasonic probe assembly relative to a manufacturing component to bisect an angle associated with the manufacturing component. The ultrasonic probe assembly may also include a surface sensing device configured to sense a curvature associated with the manufacturing component. The ultrasonic probe assembly may further include a plurality of sensors configured to measure a first displacement value associated with the centering device and a second displacement value associated with the surface sensing device. The ultrasonic probe assembly may also include an actuator configured to modify a position of an ultrasonic transducer. The systems may further include an electronics housing that may include a control circuit configured to determine a position adjustment value based on at least one of the first displacement value and the second displacement value.

In some embodiments, the centering device may include a first surface following guide, a second surface following guide, and a coupling device coupled to the first surface following guide and the second surface following guide. The coupling device may be biased by a first tension device. In some embodiments, at least one of the first displacement value and second displacement value identifies a change in the angle associated with the manufacturing component or a change in a position of the ultrasonic probe assembly relative to the manufacturing component. In various embodiments, the position adjustment value identifies a positional adjustment configured to modify a position of the ultrasonic transducer to offset the change. In some embodiments, the actuator is configured to modify the position of the ultrasonic transducer based, at least in part, on the position adjustment value to offset the change.

DETAILED DESCRIPTION

Figure 1:
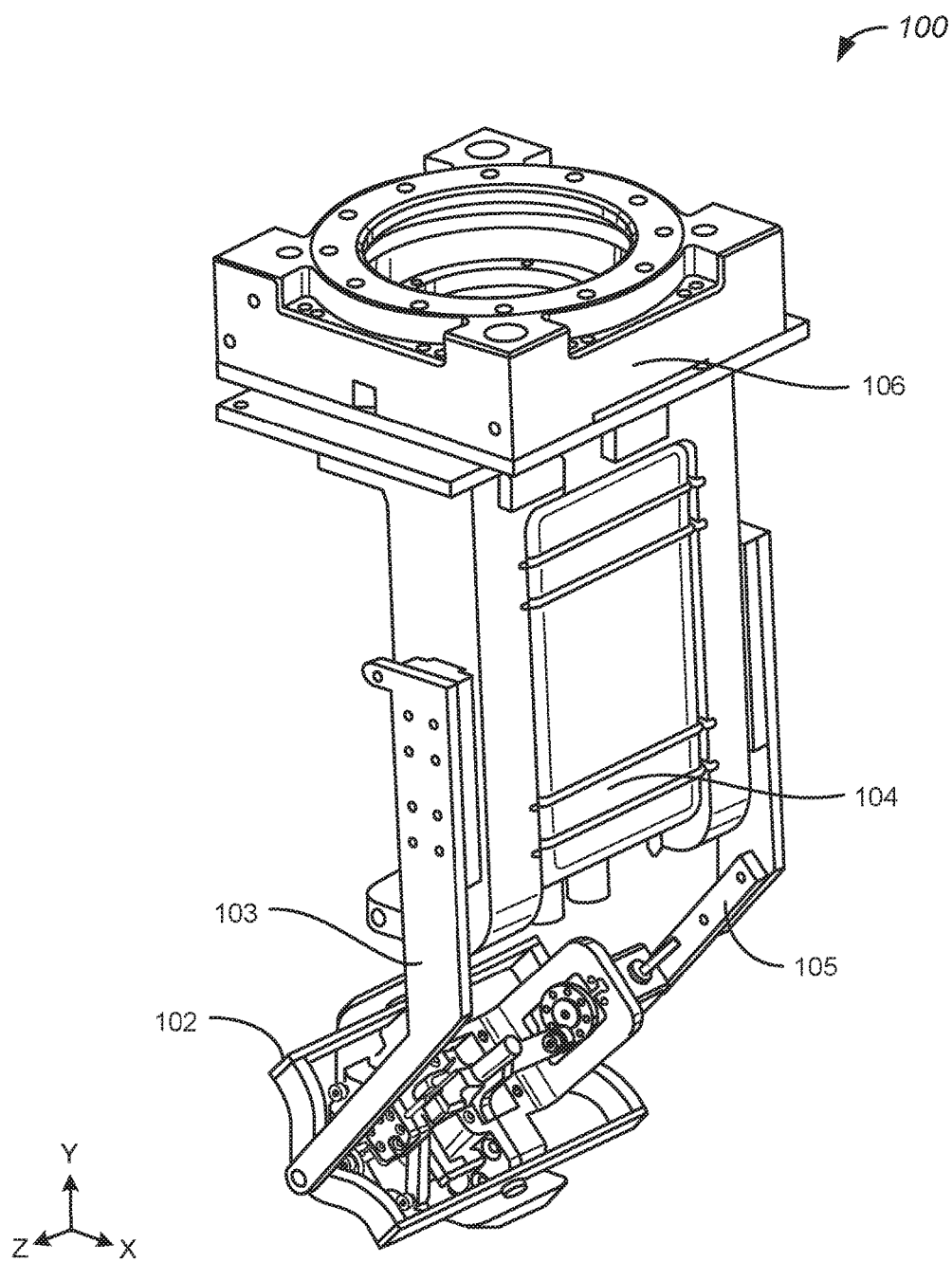
FIG. 1 illustrates an example of an ultrasonic probe assembly, configured in accordance with some embodiments.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific examples, it will be understood that these examples are not intended to be limiting.

Inspection of manufacturing components may utilize a technique such as ultrasonic non-destructive inspection (NDI). Such a technique may be utilized for non-destructive inspection of manufacturing components such as vehicle parts, which may be composite structures. Such composite structures may have particular geometries, as may be the case with particular vehicle or manufacturing parts, such as flanges. Accordingly, such parts may have portions that are scanned to measure structural and mechanical properties of the parts to ensure they are free of structural defects. Such portions may have curvatures of varying radii as well as varying angles associated with them. In such situations, a configuration of the transducer may need to be manually adjusted or a probe shoe associated with the transducer may need to be changed. Such changes may be required because the transducer must remain within a designated distance from the part being scanned for the scan to be implemented. Moreover, the transducer must be maintained at a particular angle or orientation relative to a particular position of the part, which may be defined by the scan path. Accordingly, changing the transducer shoe and making such manual changes requires additional time for inspection as well as additional inspection procedure documentation. In some instances, entirely different probes are required for different curvatures and angles. Accordingly, such scanning techniques remain limited because they utilize a relatively large amount of time, require significant manual intervention, and sometimes require numerous sets of different probes.

Various embodiments disclosed herein provide the ability to inspect a manufacturing component, such as a vehicle part, having a variable radius and variable angle with a single probe. As will be discussed in greater detail below, embodiments as disclosed herein may include a centering device and a surface sensing device that may be configured to, among other things, monitor changes in a radius and angle of a manufacturing component, and provide the basis for the generation of a position adjustment value that dynamically adjusts the position of a transducer included in the probe to dynamically compensate for changes in the radius and angle that may occur along a particular scan path associated with that manufacturing component. In this way, a single probe may be used to scan a path along a manufacturing component that has a variable radius and variable angle, and such scanning may be implemented without manual intervention such as changing transducer shoes.

FIG. 1 illustrates an example of an ultrasonic probe assembly, configured in accordance with some embodiments. An ultrasonic probe assembly, such as ultrasonic probe assembly 100, may be utilized to implement inspection scans of various vehicle parts or components. As discussed above, such scans may be utilized to ensure that the vehicle part does not include structural defects. As also, discussed above, the geometry of the vehicle part may change over the course of a scan path. Such changes may make it difficult for an ultrasonic probe assembly to implement the scan path without changing the configuration of the ultrasonic probe assembly itself, or utilizing and entirely different ultrasonic probe assembly. Accordingly, various embodiments disclosed herein provide an ultrasonic probe assembly that may dynamically compensate for changes in a radius and angle of a vehicle part within a scan path, thus enabling the use of a single ultrasonic probe assembly to implement a single scanning operation for a scan path.

In various embodiments, ultrasonic probe assembly 100 may include end effector 102 which may be configured to position and hold a transducer or a transceiver, such as an ultrasonic transducer, relative to a vehicle part, which may be a composite structure. As discussed above, the transducer may be configured to deliver energy to and/or analyze energy received from a vehicle part that is being scanned. In some embodiments, the transducer may be configured to operate in a pulse echo mode. Accordingly, the transducer may be used to implement an ultrasonic non-destructive inspection (NDI) method that may use sound energy traveling through the vehicle part to detect and identify any defects or flaws that may be present within the part. As will be discussed in greater detail below, such an inspection method may be implemented at portions of vehicle parts that may be composite structures. Moreover, as will be discussed in greater detail below, as dimensional properties of the portions change, one or more components of end effector 102 may be configured to dynamically adjust the position of the transducer/transceiver to compensate for the changes, ensure proper placement of the transducer/transceiver, and ensure that the scanning of the vehicle part may continue. As shown in FIG. 1, end effector 102 may be coupled with other components of ultrasonic probe assembly 100 via various support members or structures, such as first portion 103 and second portion 105 of ultrasonic probe assembly 100.

Ultrasonic probe assembly 100 may also include housing 104 which may be configured to house one or more components of probe assembly 100. For example, housing 104 may house various electronics associated with probe assembly 100. As will be discussed in greater detail below with reference to FIG. 6, housing 104 may include a power supply, sensor electronics, and a control circuit. Accordingly, housing 104 may include electrical and computational hardware and software that may be configured to enable the movement and positioning of the transducer. As will be discussed in greater detail below, electronics and a control circuit included in housing 104 may be configured to control the movement and positioning of the transducer dynamically and during operation of the transducer, thus enabling dynamic repositioning of the transducer to compensate for changes in a radius of a curvature of the vehicle part as well as an angle relative to the transducer.

In various embodiments, ultrasonic probe assembly 100 may further include interface 106 which may be configured to provide mechanical and/or electrical coupling between end effector 102 and housing 104, and various other components that may be implemented in a manufacturing and testing environment, such as a robotic arm. Accordingly, interface 106 may be configured to provide mechanical coupling between ultrasonic probe assembly 100 and the robotic arm such that the robotic arm may move ultrasonic probe assembly 100 along a scanning path associated with a vehicle part or component, as will be discussed in greater detail below with reference to FIG. 3.

Figure 2:
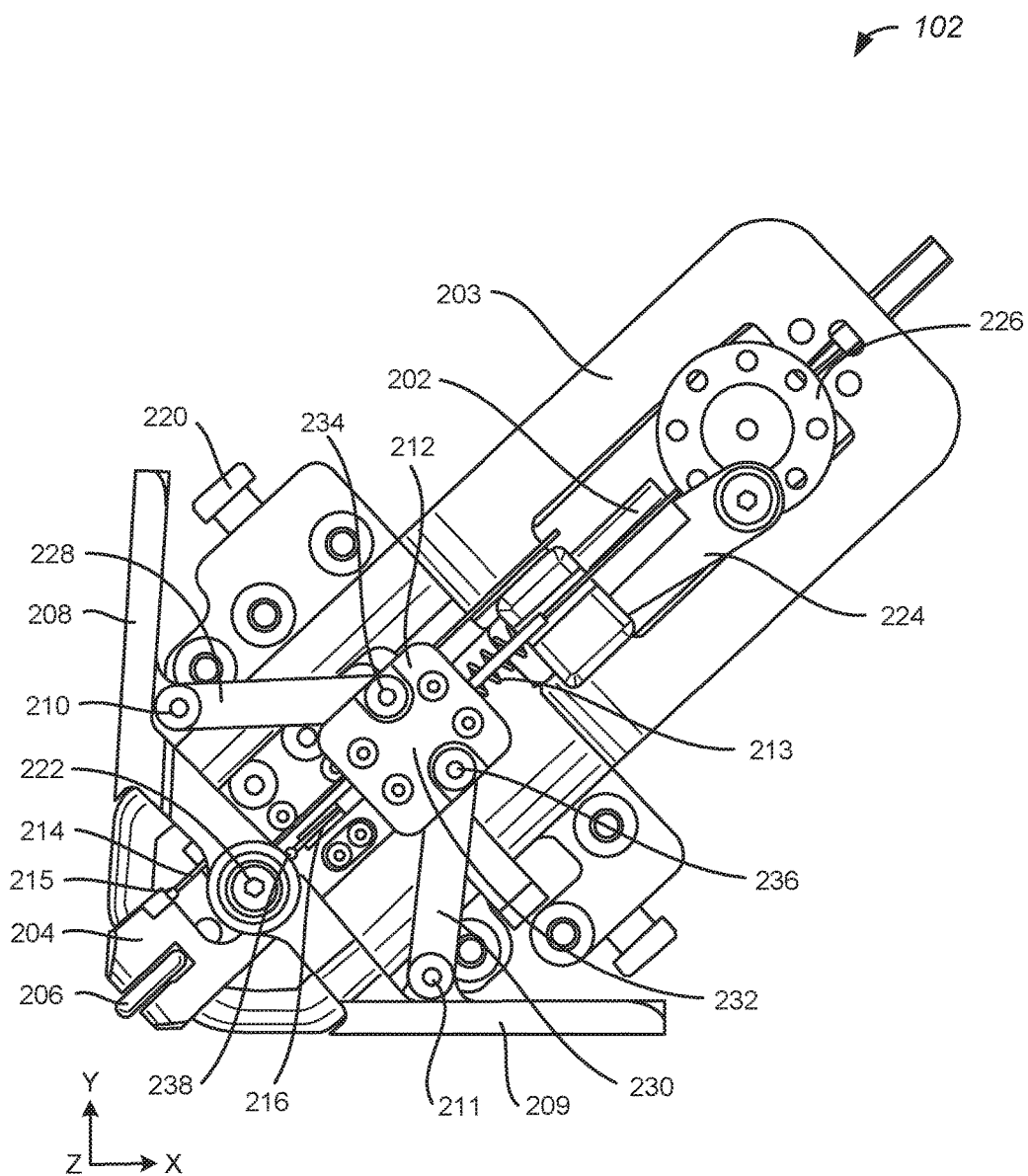
FIG. 2 illustrates an example of an end effector of an ultrasonic probe assembly, configured in accordance with some embodiments.

FIG. 2 illustrates an example of an end effector of an ultrasonic probe assembly, configured in accordance with some embodiments. As discussed above, ultrasonic probe assemblies may be utilized to implement inspection scans of various vehicle parts or components. As will be discussed in greater detail below, ultrasonic probe assemblies as discussed herein may dynamically compensate for changes in a radius and angle of a vehicle part within a scan path, thus enabling the use of a single ultrasonic probe assembly to implement a single scanning operation for a scan path. Accordingly, embodiments as disclosed herein may include surface sensing devices and centering devices that enable monitoring of such changes, and the generation of position adjustment values to modify a position of a transducer to compensate for such changes.

In various embodiments, end effector 102 may include support member 203 which may be configured to provide mechanical coupling and support for various other components of end effector 102, such as transducer 202, surface sensing device 204, and centering device 212 discussed in greater detail below. Accordingly, various components may be coupled to support member 203, and to each other via support member 203.

In various embodiments, end effector 102 may include surface sensing device 204 which may be configured to sense and identify one or more properties of a curvature associated with a vehicle part, such as its radius, that is being scanned. Accordingly, surface sensing device 204 may be configured to follow or track a surface of the vehicle part, as will be discussed in greater detail below with reference to FIG. 3, and may be configured to determine a relative distance offset from the surface of the vehicle component and another component of end effector 102, such as transducer 202. For example, surface sensing device 204 may include one or more wheels, such as wheel 206, which may be configured to enable motion in a particular direction along the surface of a vehicle part that is being scanned. In this example, wheel 206 may roll along the surface as the scan is performed. Moreover, surface sensing device 204 may be configured to move or permit an amount of distance travel in response to a surface of the vehicle part changing position, radius of curvature, or angle relative to end effector 102. In some embodiments, surface sensing device 204 may be biased by a tension device, such as a spring, that enables such travel responsive to pressure applied by the vehicle part surface, which may cause compression of the tension device when the surface of the radius comes closer to end effector 102, and further enables surface sensing device 204 to return to a resting position when such pressure is not present. In this way, surface sensing device 204 may be configured to follow or track a relative position of a surface of a vehicle part being scanned.

Moreover, surface sensing device 204 may be coupled to first sensor 214 which may be configured to determine a distance offset or travel associated with surface sensing device 204 and provide such determined distance to one or more other components, such as a control circuit discussed in greater detail below. In various embodiments, first sensor 214 may be a transducer or transformer such as a differential variable reluctance transformer (DVRT). In various embodiments, first sensor 214 may be coupled to surface sensing device 204 via first interface 215, and may be configured to detect changes in a position of surface sensing device 204. Accordingly, changes in a position of surface sensing device 204 and first interface 215 may be transformed into a first signal generated by first sensor 214, as well as associated electronics discussed in greater detail below, and provided to one or more other components such as a control circuit associated with end effector 102.

According to various embodiments, end effector 102 may also include centering device 212 which may be configured to modify or adjust a position and relative angle of one or more components of end effector 102 relative to the vehicle part being scanned. As will be discussed in greater detail below with respect to FIG. 3, as a scan is performed and end effector 102 is moved along a scan path, a radius of the curvature of the vehicle part as well as a relative angle of end effector 102 to the vehicle part may change. Accordingly, centering device 212 may be configured to modify a position of end effector 102 to ensure that the angle at which end effector 102 as well as various other components of end effector 102, such as transducer 202, are positioned relative to the portion of the vehicle part at an angle that bisects the angle of the portion. In this way, centering device 212 may be configured to adjust a position of end effector 102 to ensure that surface sensing device 204 and transducer 202 are centered relative to a portion of the vehicle part that is being scanned.

Centering device 212 may include first surface following guide 208 and second surface following guide 209 which may be configured to contact and identify a location of a first and second surfaces of the vehicle part being scanned. As discussed in greater detail below with respect to FIG. 3, the first and second surfaces may be on different sides of the portion being scanned. In various embodiments, first surface following guide 208 and second surface following guide 209 may be coupled to first arm 228 and second arm 230 via first joint 210 and second joint 211 respectively. Furthermore, first arm 228 and second arm 230 may be coupled to coupling housing 232 via third joint 234 and fourth joint 236 respectively. Moreover, centering device 212 may include tension device 213 which may be coupled with coupling housing 232 and may be configured to bias coupling housing 232 in a first direction. When configured in this way, force applied by tension device 213 may push against coupling housing 232 and first surface following guide 208 and second surface following guide 209 via first arm 228 and second arm 230.

Moreover, end effector may allow free rotation by, for example, first rotation point 220 and second rotation point 222, to enable the position of end effector to stabilize such that the force applied by tension device 213 is split evenly amongst first arm 228 and second arm 230. In this way, end effector 102 may be positioned such that equal force is applied by tension device 213 via first arm 228 and second arm 230. As will be described in greater detail below with reference to FIG. 3, changes in a position of first surface following guide 208 or second surface following guide 209, which may be caused by a change in a position of a surface of a vehicle part being scanned, may cause centering device 212 to adjust a position of end effector to reestablish equilibrium between the forces applied via first arm 228 and second arm 230. In doing so, end effector 102 may be positioned to bisect the angle of a portion that joins the surfaces currently contacting first surface following guide 208 or second surface following guide 209. In this way, centering device 212 may dynamically adjust a position of end effector 102 to maintain equilibrium between forces applied via first arm 228 and second arm 230, and to bisect the angle of portion that joins the surfaces currently contacting first surface following guide 208 or second surface following guide 209.

Furthermore, centering device 212 may be coupled to second sensor 216. As similarly discussed above with reference to first sensor 214, second sensor 216 may be a transducer or transformer such as a differential variable reluctance transducer (DVRT). Accordingly, centering device 212 may be coupled to second sensor 216 via second interface 238, and second sensor 216 may be configured to detect changes in a position of centering device 212. Accordingly, changes in a position of centering device 212 and second interface 238 may be transformed into a second signal generated by second sensor 216, as well as associated electronics discussed in greater detail below, and provided to one or more other components such as a control circuit associated with end effector 102. As will be discussed in greater detail below, the control circuit may be configured to generate one or more position adjustment values based on the first and second signals.

In various embodiments, end effector 102 may also include actuator 226 which may be coupled to transducer 202 via lever 224. In various embodiments, actuator 226 may be configured to modify a position of transducer 202. Accordingly, as will be discussed in greater detail below, first sensor 214 and second sensor 216 may be used to generate a first signal and a second signal which may characterize a position, angle, and distance relative to a surface of a portion of a vehicle part being scanned. In various embodiments, one or more components, such as the control circuit, may be configured to generate a position adjustment value based on the first signal and the second signal. The position adjustment value may be used by actuator 226 to move a position of transducer to compensate for and counteract a change in position, angle, and/or distance determined by the first and second signals. Accordingly, actuator 226 may be a servo motor that may be configured to move transducer 202 via lever 224. In one example, if it is determined that transducer has moved farther away from the surface of the portion being scanned, an position adjustment value may be generated that may configure actuator 226 to move transducer 202 closer to the surface of the portion thus offsetting the distance displacement. Accordingly, actuator 226 may be configured to determine and adjust a distance between transducer 202 and surface that is being scanned.

Figure 3:
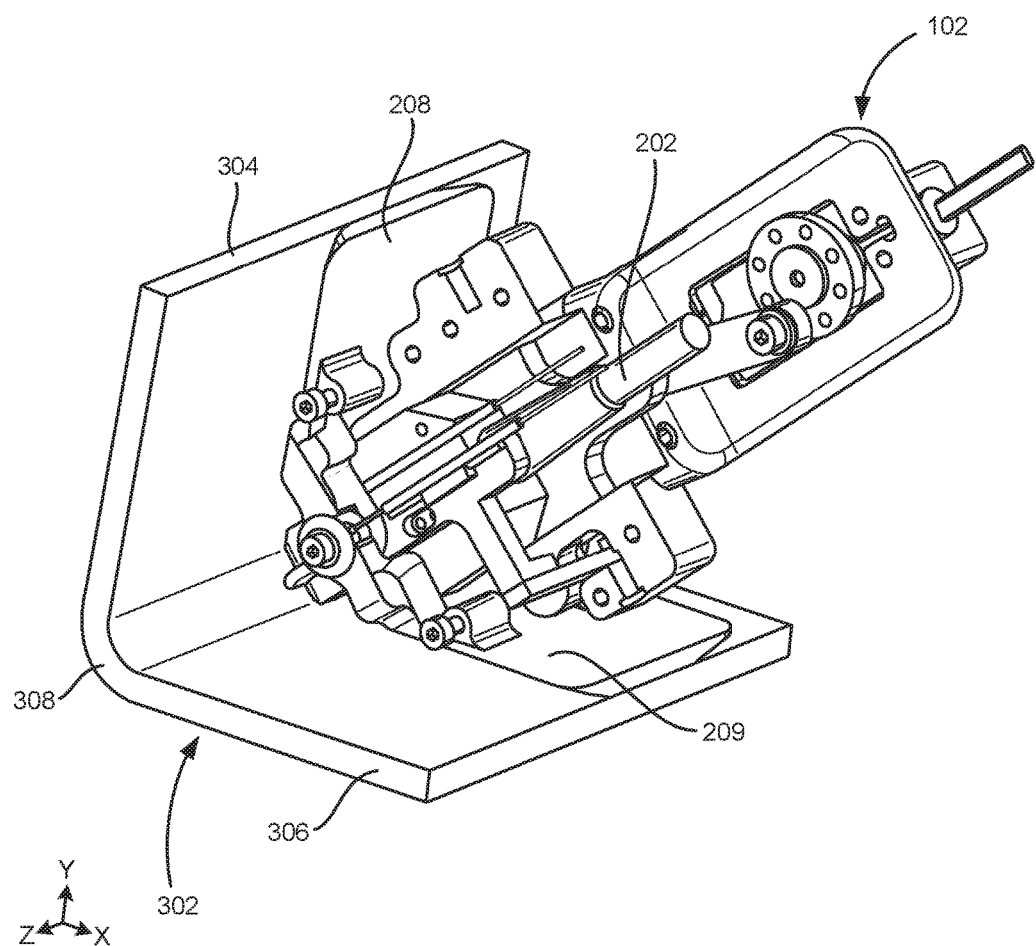
FIG. 3 illustrates an example of an end effector of an ultrasonic probe assembly scanning a vehicle part, configured in accordance with some embodiments.

FIG. 3 illustrates an example of an end effector of an ultrasonic probe assembly scanning a vehicle part, configured in accordance with some embodiments. As shown in FIG. 3, end effector 102 may be scanning a vehicle part, such as vehicle part 302. As discussed above, vehicle part 302 may be a composite structure undergoing scans to identify any structural defects that may be present. In some embodiments, vehicle part 302 may have first surface 304 and second surface 306 which may be coupled via portion 308 which may have a particular radius of curvature in a first direction as well as an angle in a second direction. For example, vehicle part 302 may be a portion of a flange. In some embodiments, portions of the flange may have a varying radius of curvature as well as a varying angle of the flange. In on example, the curvature may be along the Z axis shown in FIG. 3, and the angle may be along the XY plane. Thus, portion 308 might not be flat in a first direction, which may be parallel to the direction of wheels, such as wheel 206, but might instead have a radius of curvature that may be associated with a circular geometry of a flange. Moreover, portion 308 may have an angle as defined by the intersection angle between first surface 304 and second surface 306.

As discussed above, during scanning, both the radius of curvature and the angle may change as vehicle part 302 may have a shape or geometry that varies. Accordingly, such changes may cause changes in the position of surface sensing device 204 and centering device 212 which may be relayed to a control circuit by first sensor 214 and second sensor 216. For example, an angle between first surface 304 and second surface 306 may change during a scan and may decrease. Accordingly, a position of first surface following guide 208 and second surface following guide 209 may change to match first surface 304 and second surface 306, a position of end effector 102 may be modified to bisect the new angle, and the change may be identified and relayed to a control circuit by first sensor 214. Moreover, the control circuit may generate a position adjustment value that may offset any change in a relative position of transducer 202, as may have occurred by an increase in distance of transducer from vehicle part 302, due to the change in angle. Moreover, as discussed above, a similar position adjustment value may be generated for a change in a radius of a curvature of portion 308.

Figure 4:
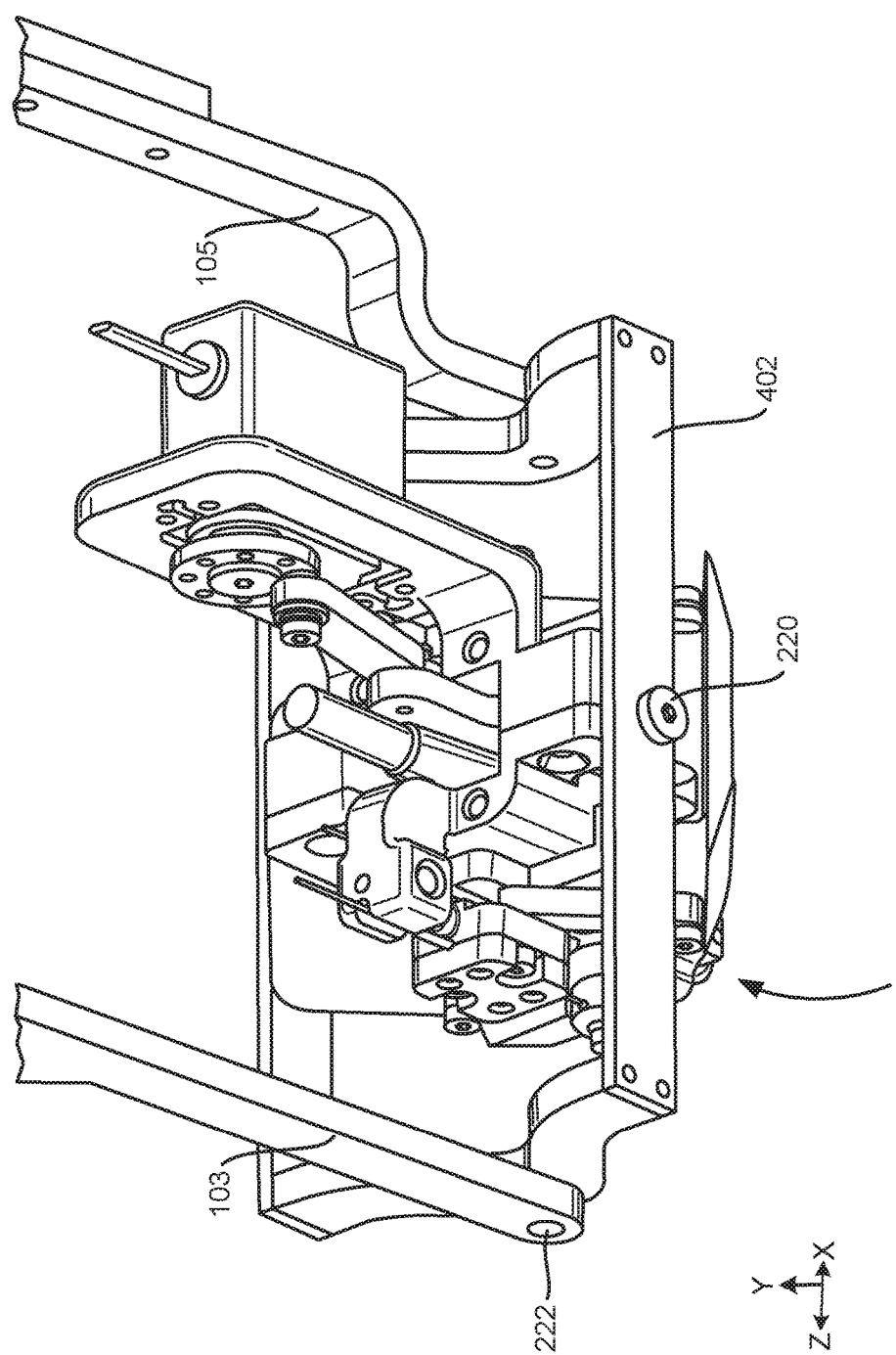
FIG. 4 illustrates another example of an end effector of an ultrasonic probe assembly, configured in accordance with some embodiments.

FIG. 4 illustrates another example of an end effector of an ultrasonic probe assembly, configured in accordance with some embodiments. As shown in FIG. 4, end effector 102 may be coupled to ultrasonic probe assembly 100 via bracket 402 as well as first portion 103 and second portion 105. Furthermore, as noted above, end effector 102 may be coupled via first rotation point 220 and second rotation point 222 which may each be any suitable rotatable joint. As shown in FIG. 4, first rotation point 220 may enable rotation in a first direction, while second rotation point enables rotation in a second direction. Accordingly, in conjunction, first rotation point 220 and second rotation point 222 enable movement of end effector 102 to follow and track changes in a radius of a curvature and an angle associated with a portion of a vehicle part being scanned. For example, rotation in a first direction enabled by first rotation point 220 may enable surface sensing device 204 to follow changes in a radius of the curvature being scanned. Moreover, rotation in a second direction enable by second rotation point 222 may enable centering device 212 to adjust to changes in the angle of the part and ensure that the transducer is oriented to bisect the angle. In this way, first rotation point 220 and second rotation point 222 may facilitate the positioning of end effector 102 during scanning of a vehicle part.

Figure 5:
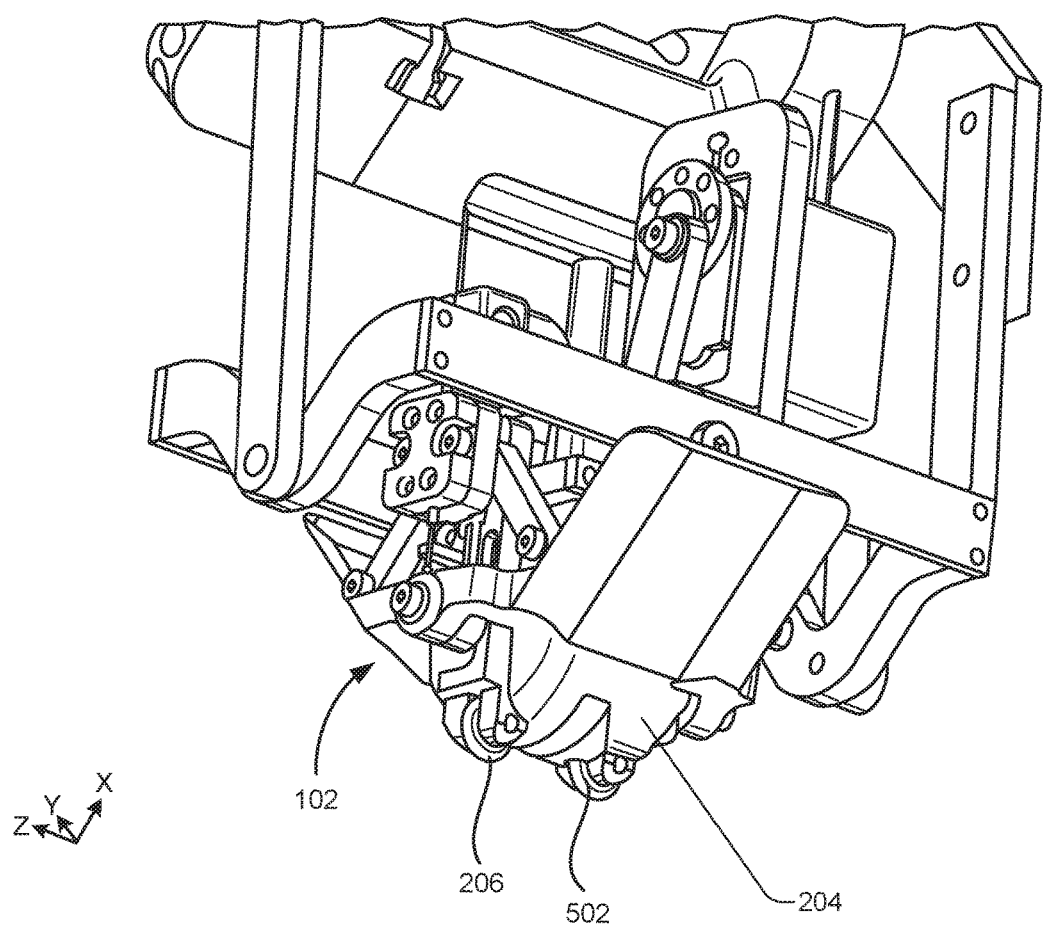
FIG. 5 illustrates yet another example of an end effector of an ultrasonic probe assembly, configured in accordance with some embodiments.

FIG. 5 illustrates yet another example of an end effector of an ultrasonic probe assembly, configured in accordance with some embodiments. FIG. 5 provides an additional view in which additional details of end effector 102 and surface sensing device 204 are visible. For example, as discussed above, surface sensing device 204 may include various components, such as wheels, which may contact a surface of a portion of a vehicle part and may follow a surface of the portion during scanning of the vehicle part. As shown in FIG. 5, surface sensing device 204 may include multiple wheels. For example, surface sensing device 204 may include wheel 206 and wheel 502. Accordingly, multiple wheels may be used to track the surface of a manufacturing component. In various embodiments, when configured in this way, changes in a radius of a curvature of the manufacturing component or vehicle part may be identified and detected with greater accuracy.

Figure 6:
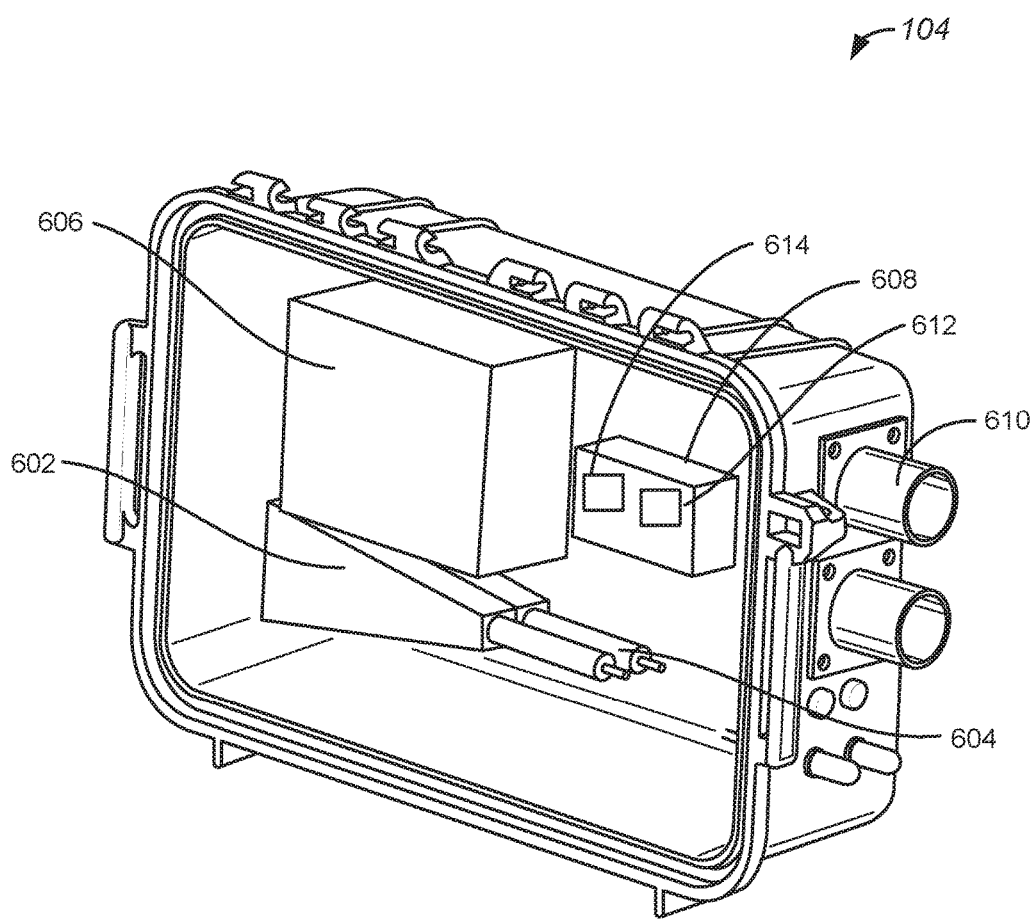
FIG. 6 illustrates an example of an electronics housing, configured in accordance with some embodiments.

FIG. 6 illustrates an example of an electronics housing, configured in accordance with some embodiments. As discussed above, an electronics housing, such as housing 104, may include various control circuits that may be used to generate an output signal that controls a positioning of a transducer to compensate for dynamic changes in a radius and angle associated with a portion of a vehicle part.

Thus, according to various embodiments, housing 104 may include first sensor electronics 602 which may be associated with first sensor 214. Accordingly, first sensor electronics 602 may be configured to monitor and track a displacement of first sensor 214, and may be further configured to generate the first signal based on the tracked displacement. In this way, first sensor electronics 602 may be configured to convert a detected motion or displacement associated with first sensor 214 into an electrical signal that may be processed by control circuit 608 discussed in greater detail below. Similarly, housing 104 may further include second sensor electronics 604 which may be associated with second sensor 216 which may be configured to convert a detected motion or displacement associated with second sensor 216 into an electrical signal that may be processed by control circuit 608.

In various embodiments, housing 104 may include control circuit 608 which may be configured to generate an output signal based on the first signal and second signal associated with first sensor 214 and second sensor 216 respectively. In various embodiments, the output signal may characterize one or more position adjustment values. Accordingly, the output signal may configure one or more components, such as actuator 226 and lever 224, to implement a positional offset defined by the position adjustment value. More specifically, the first signal may characterize a first distance from the surface of the portion being scanned to the transducer, as determined by a displacement of first sensor 214 associated with surface sensing device 204. Moreover, the second signal may characterize a second distance associated with the angle of portion that is displacing end effector 102.

In various embodiments, control circuit 608 may be configured to generate the output signal based on a combination of the first signal and the second signal. In various embodiments, first sensor 214 and second sensor 216 may each include analog to digital converters and may be configured to generate streams of binary data values based on their respective sensor information. Accordingly, control circuit 608 may be configured to generate an output signal that includes one or more position adjustment values based on those data values.

In one example, the various equations described below may be implemented to determine position adjustment values and generate an output signal based on such position adjustment values. As discussed above, first and second sensors 214 and 216 may generate streams of data values, which may be represented as DVRTal1 and DVRTal2 below. Such data values may be modified by a ratio specific to the sensors to facilitate determination of the position adjustment values. For example, first and second sensors 214 and 216 may be DVRTs having a size of 6 mm (0.2362 inches) and 10-bit analog to digital converters (1023). Accordingly a ratio may be determined by equation 1:

$$\text{ratio} = 0.2362204724 / 1023.0 \tag{1}$$

Adjusted measurements may be determined by applying the ratio to the data values as shown in equations 2 and 3 below:

$$\text{DVRT1} = \text{DVRTV}al1 * \text{ratio} \tag{2}$$

$$\text{DVRT2} = \text{DVRTV}al2 * \text{ratio} \tag{3}$$

These measured distances may be used to determine a current angle (Y) associated with the transducer, as shown in equation 4:

$$Y = (69.59521602 * \text{DVRT2}^2) + (77.39453778 * \text{DVRT2}) + 84.07525908 \tag{4}$$

The angle may be used to determine adjustment values which may represent a desired position of the transducer (which may also represent a desired distance from the surface being scanned), and a difference between the desired position and the current position. In some embodiments, the angle may be used to determine a desired position of the sensor, as shown in equations 5, 6, and 7 below where "adj" represents a desired adjustment determined based on the angle Y, "Madj" represents a mechanical offset adjustment associated with first sensor 214, and "DVRT1$n$" represents the desired position of the sensor tip or interface of first sensor 214.

$$\text{adj} = -0.00006516 * Y^2 + 0.01770932 * Y - 1.04068426 \tag{5}$$

$$M\text{adj} = 0.352665 * \text{DVRT1} - 0.02821 \tag{6}$$

$$\text{DVRT1}n = \text{DVRT1} - \text{adj} + M\text{adj} \tag{7}$$

In some embodiments, actuator 226 may include a camshaft that may be rotated to modify a position of transducer 202 coupled to actuator 226. Accordingly, a cam ratio formula may be implemented to determine a rotational angle to be applied to the camshaft to modify the position of transducer 202. Thus, the position adjustment value may be an angle of rotation. The angle of rotation (W) may be determined by equations 8, 9, and 10 shown below, where X represents a desired distance travel of transducer 202, and Z represents the cam ratio:

$$Z = 0.000024639483 \ast Y^3 - 0.005475734839 \ast Y^2 + 0.458658510293 \ast Y - 11.47347235 \quad (8)$$

$$X = Z \ast DVRT1n \quad (9)$$

$$W = 6180.10566878 \ast X^6 - 10337.90991926 \ast X^5 + 5527.37175465 \ast X^4 - 404.83747172 \ast X^3 - 524.2298389 \ast X^2 + 296.04537675 \ast X + 16.18367626 \quad (10)$$

In various embodiments, control circuit 608 may be implemented in a reprogrammable logic device. Accordingly, control circuit 608 may be implemented as circuitry or processing logic included in a field programmable gate array (FPGA) configured to implement the determinations discussed above. In some embodiments, control circuit 608 may be implemented as one or more integrated circuits (IC's) or application specific ICs (ASICs) that are configured to implement the determinations discussed above. Moreover, control circuit 608 may be configured to include processor 612 implemented as discussed above, as well as memory 614. In various embodiments, memory 614 may be a non-volatile memory device configured to store positional data associated with the first and second signals as well as offset data associated with the output signal.

In various embodiments, housing 104 may also include power supply 606 which may be configured to generate power to power all components within housing 104. Housing 104 may also include various ports and connections, such as communications port 610, which may enable communication with components outside of housing 104. For example, communications ports may be provided to communicatively couple control circuit 608 with actuator 226, and couple sensor electronics with sensors. In various embodiments, communications port 610 may also be configured to provide manual control via "text" commands. Such implementation of text commands may facilitate the inspection of nonconcentric radii and provide a "hand tuning" option that may be used for special inspections.

Figure 7:
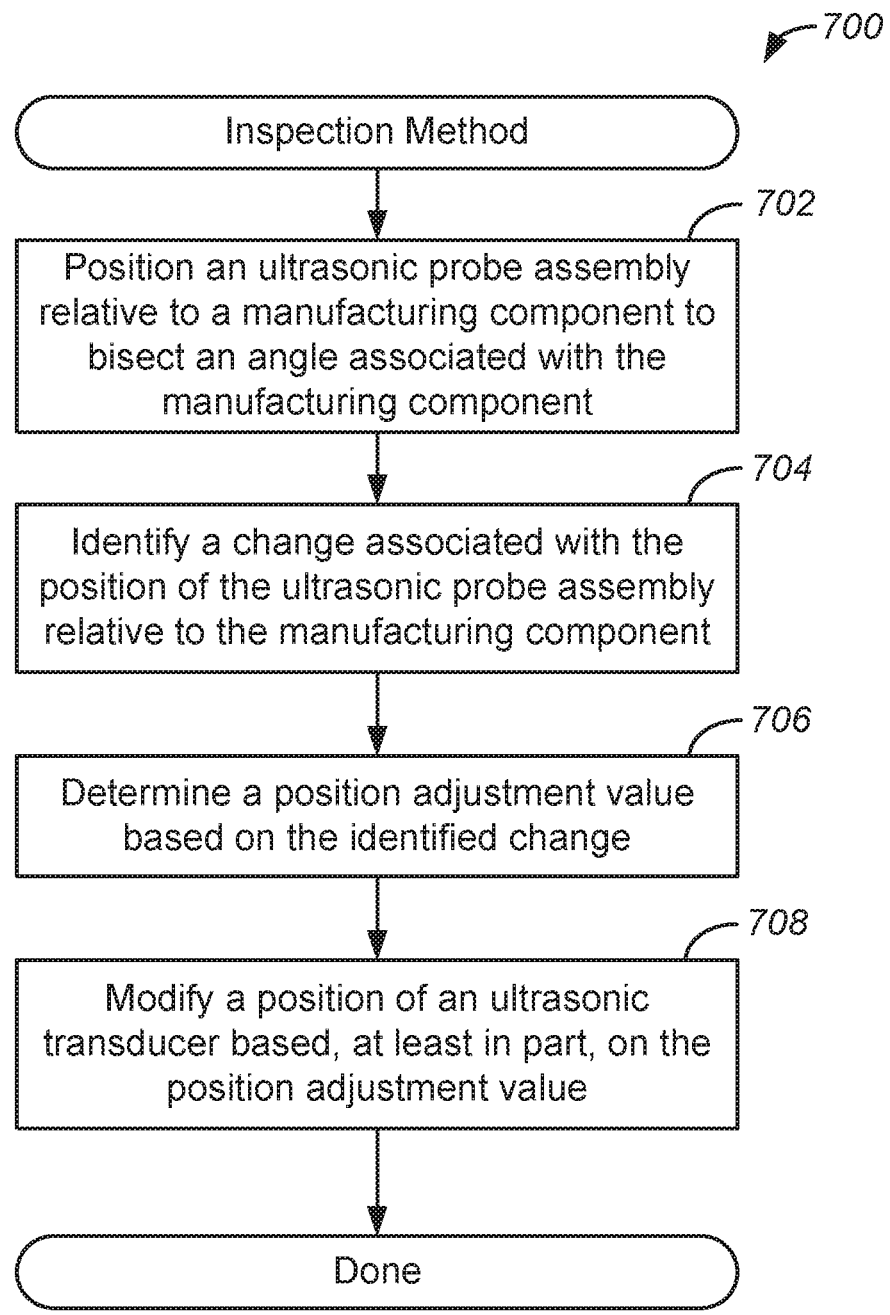
FIG. 7 illustrates a flow chart of an example of a method for inspecting of a manufacturing component, implemented in accordance with some embodiments.

FIG. 7 illustrates a flow chart of an example of a method for inspecting a manufacturing component, implemented in accordance with some embodiments. As will be discussed in greater detail below, changes in a radius and angle of a portion of a manufacturing component, also referred to herein as a vehicle part, may be detected and identified dynamically. Moreover, position adjustment values may be generated that dynamically compensate for such changes. In this way, a scanning path having a variable radius of curvature and variable angle along a particular portion of a manufacturing component may be scanned using a single probe assembly that dynamically compensates for such changes.

Method 700 may commence with operation 702 during which an ultrasonic probe assembly may be positioned relative to a manufacturing component to bisect an angle associated with the manufacturing component. As discussed above, during inspection of the manufacturing component, which may be a vehicle part, an end effector of the ultrasonic probe assembly may be positioned along a particular portion of the manufacturing component that may define a scanning path for the ultrasonic probe assembly. Accordingly, the ultrasonic probe assembly may be positioned, and scanning of the manufacturing component may be initiated.

Method 700 may proceed to operation 704 during which a change associated with the position of the ultrasonic probe assembly relative to the manufacturing component may be identified. As discussed above, the change may be due to a change in the radius or angle of the portion being scanned, and such a change may be identified or determined based on one or more sensors, such as the first sensor and the second sensor discussed above. Moreover, such a change may occur dynamically during the scanning process.

Method 700 may proceed to operation 706 during which a position adjustment value may be determined based on the identified change. Accordingly, a component, such as the control circuit may be configured to generate the position adjustment value based on the identified change. As discussed above, such a position adjustment value may be determined based on displacement information provided by various sensors implemented within the ultrasonic probe assembly, and used to characterize the identified change.

Method 700 may proceed to operation 708 during which a position of a transducer based may be modified, at least in part, on the position adjustment value. Accordingly, a component, such as an actuator, may utilize the position adjustment value to implement one or more changes in a position of the transducer. In various embodiments, implementation of the position adjustment value may compensate for the change identified at operation 704. Accordingly, a change that may otherwise effect and degrade the ability of the transducer to scan the manufacturing component may be compensated for such that the change does not effect and degrade the ability of the transducer, and enables the scan to continue despite a variety of changes associated with the manufacturing component that may occur.

Figure 8:
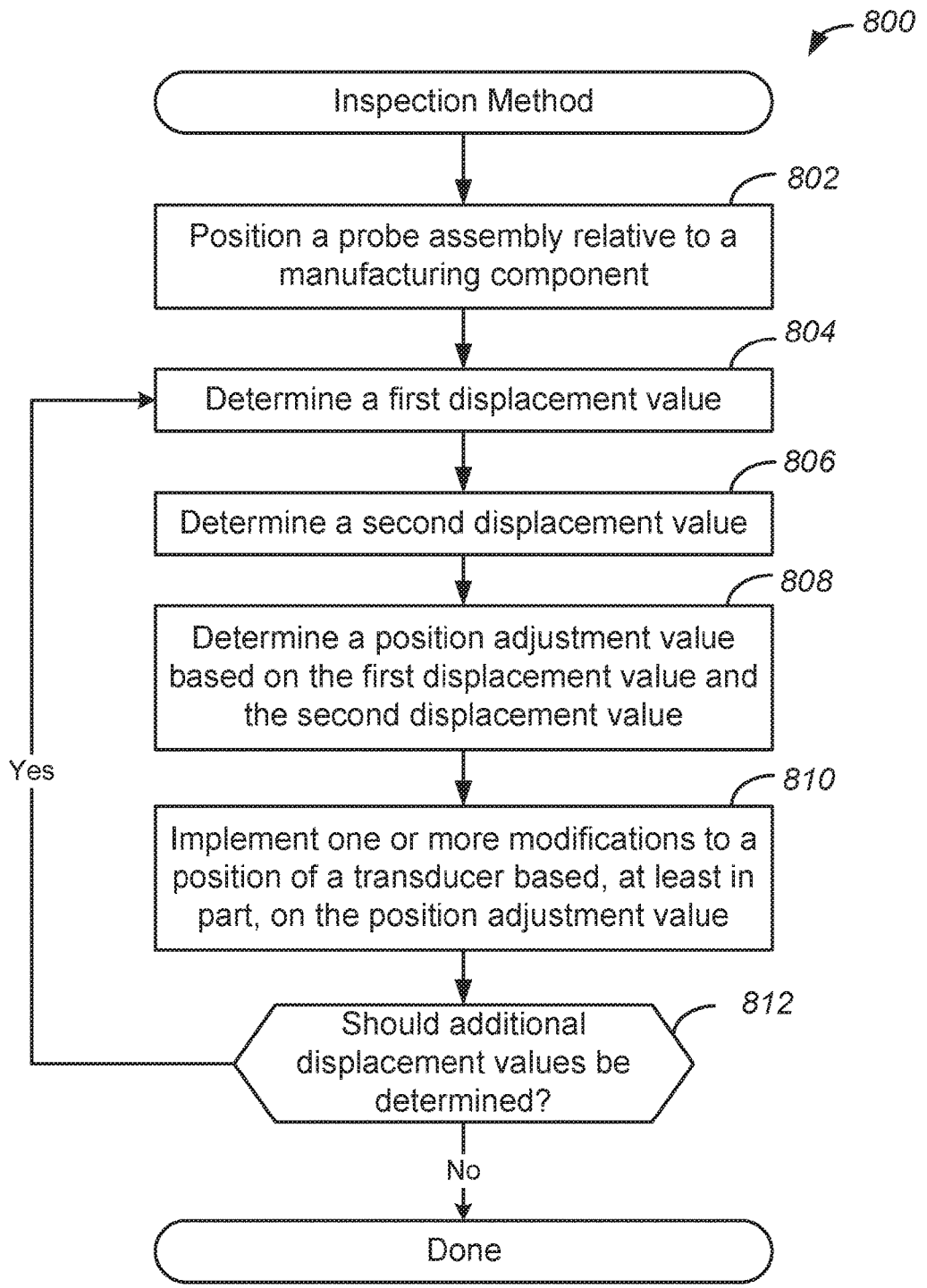
FIG. 8 illustrates a flow chart of another example of a method for inspecting a manufacturing component, implemented in accordance with some embodiments.

FIG. 8 illustrates a flow chart of another example of a method for inspecting a manufacturing component, implemented in accordance with some embodiments. As similarly discussed above, changes in a radius of curvature and an angle associated with a manufacturing component may be detected and identified dynamically, and position adjustment values may be generated that dynamically compensate for such changes. Accordingly, a scanning path having a variable radius and variable angle along a particular portion may be scanned using a single probe assembly that dynamically compensates for such changes.

Method 800 may commence with operation 802 during which a probe assembly may be positioned relative to a manufacturing component. As similarly discussed above, a probe assembly may be positioned relative to a manufacturing component to implement an inspection scan of the manufacturing component. In some embodiments, positioning of the probe assembly may include positioning the end effector such that an angle associated with a portion of the manufacturing component included in the scan path is bisected. As discussed above, the end effector of the ultrasonic probe assembly may be positioned along a particular portion of the manufacturing component that may define a scanning path for the ultrasonic probe assembly. Accordingly, the ultrasonic probe assembly may be positioned, and scanning of the manufacturing component may commence.

Method 800 may proceed to operation 804 during which a first displacement value may be identified. In various embodiments, the first displacement value may be determined by a first sensor as well as associated first sensor electronics. For example, a displacement or movement of a surface sensing device may cause a displacement of the first sensor. As discussed above, the displacement of the surface sensing device may be due to a change in a radius of a curvature being measured as well as a change in a distance from the end effector to the surface of the manufacturing component. In some embodiments, the displacement of the first sensor may be detected by the first sensor electronics and used to generate a first displacement value.

Method 800 may proceed to operation 806 during which a second displacement value may be identified. According to some embodiments, the second displacement value may be determined by a second sensor as well as associated second sensor electronics. As discussed above, a displacement or movement of a centering device may cause a displacement of the second sensor. As discussed above, the displacement of the centering device may be due to a change in an angle of the portion being scanned as well as a change in a distance from the end effector to the surface of the portion. In some embodiments, the displacement of the second sensor may be detected by the second sensor electronics and used to generate a second displacement value.

Method 800 may proceed to operation 808 during which a position adjustment value may be determined based on the first displacement value and the second displacement value. As discussed above, a component, such as the control circuit, may be configured to generate the position adjustment value based on the first displacement value and the second displacement value. Accordingly, the control circuit may determine the position adjustment value and generate an output signal that includes or characterizes the position adjustment value. In various embodiments, the output signal may be provided to another component, such as an actuator, via one or more communications ports.

Method 800 may proceed to operation 810 during which one or more modifications to a position of a transducer may be implemented based, at least in part, on the position adjustment value. As similarly discussed above, a component, such as an actuator, may utilize the position adjustment value to implement one or more changes in a position of the transducer, and the implementation of the position adjustment value may compensate for displacements identified during operations 804 and 806. Accordingly, changes may be compensated for such that the changes do not effect and degrade the ability of the transducer to implement the scan. Furthermore, implementation of the position adjustment value may enable the scan to continue despite a variety of changes associated with the manufacturing component that may occur.

Method 800 may proceed to operation 812 during which it may be determined whether additional displacement values should be determined. Such a determination may be made based on an overall status indicator associated with the scan. For example, the end effector may be moved to various positions or locations in a scan path, as may be determined by one or more systems controlling the robotic arm associated with the end effector. Accordingly, if the scan has reached the end of the scan path, then no more measurements need to be made, and it may be determined that no additional displacement values should be determined. However, if the scan has not reached the end of the scan path, and the scan is still underway, it may be determined that additional displacement values should be determined. If it is determined that additional displacement values should be determined, method 800 may return to operation 804. If it is determined that no additional displacement values should be determined, as may be the case at the termination of a scan, method 800 may terminate.

While the systems, apparatus, and methods disclosed above have been described with reference to airplanes and the aerospace industry, it will be appreciated that the embodiments disclosed herein may be applied to any other context as well, such as automotive, railroad, and other mechanical and vehicular contexts.

Figure 9:
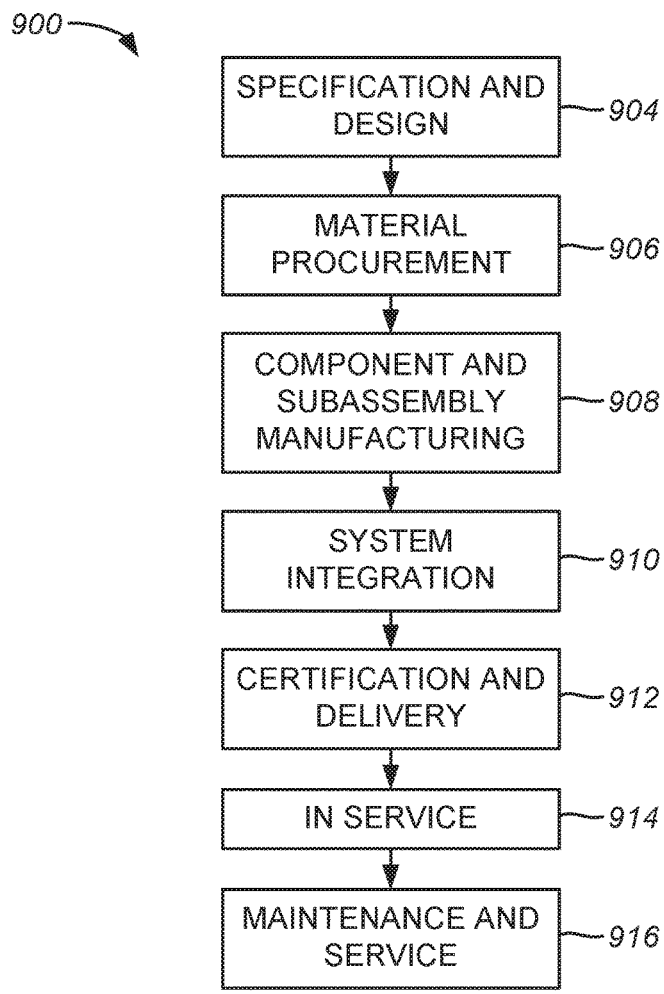
FIG. 9 illustrates a flow chart of an example of an airplane production and service methodology, in accordance with some embodiments.
Figure 10:
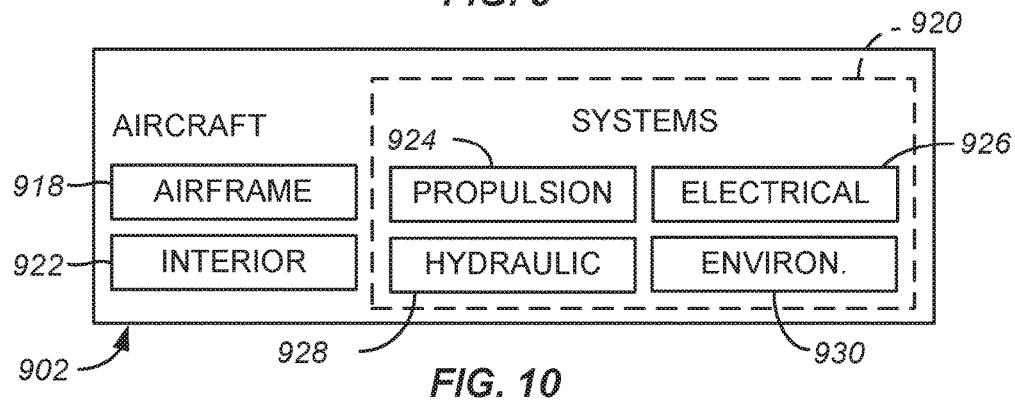
FIG. 10 illustrates a block diagram of an example of an airplane, in accordance with some embodiments.

Accordingly, embodiments of the disclosure may be described in the context of an airplane manufacturing and service method 900 as shown in FIG. 9 and an airplane 902 as shown in FIG. 10. During pre-production, illustrative method 900 may include specification and design 904 of the airplane 902 and material procurement 906. During production, component and subassembly manufacturing 908 and system integration 910 of the airplane 902 takes place. Thereafter, the airplane 902 may go through certification and delivery 912 in order to be placed in service 914. While in service by a customer, the airplane 902 is scheduled for routine maintenance and service 916 (which may also include modification, reconfiguration, refurbishment, and so on).

Each of the processes of method 900 may be performed or carried out by a system integrator, a third party, and/or an operator (e.g., a customer). For the purposes of this description, a system integrator may include without limitation any number of airplane manufacturers and major-system subcontractors; a third party may include without limitation any number of venders, subcontractors, and suppliers; and an operator may be an airline, leasing company, military entity, service organization, and so on.

As shown in FIG. 10, the airplane 902 produced by illustrative method 900 may include an airframe 918 with a plurality of systems 920, and an interior 922. Examples of high-level systems 920 include one or more of a propulsion system 924, an electrical system 926, a hydraulic system 928, and an environmental system 930. Any number of other systems may be included. Although an aerospace example is shown, the principles of the invention may be applied to other industries, such as the automotive industry.

Apparatus and methods embodied herein may be employed during any one or more of the stages of the production and service method 900. For example, components or subassemblies corresponding to production process 908 may be fabricated or manufactured in a manner similar to components or subassemblies produced while the airplane 902 is in service. Also, one or more apparatus embodiments, method embodiments, or a combination thereof may be utilized during the production stages 908 and 910, for example, by substantially expediting assembly of or reducing the cost of an airplane 902. Similarly, one or more of apparatus embodiments, method embodiments, or a combination thereof may be utilized while the airplane 902 is in service, for example and without limitation, to maintenance and service 916.

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatus. Accordingly, the present examples are to be considered as illustrative and not restrictive.

What is claimed is:

1. A device comprising:
   a centering device configured to modify a position of an ultrasonic probe assembly relative to a manufacturing component to bisect an angle associated with the manufacturing component, the ultrasonic probe assembly comprising an ultrasonic transducer;
   a surface sensing device configured to sense a curvature associated with the manufacturing component;
   a plurality of sensors configured to measure a first displacement value associated with the centering device and a second displacement value associated with the surface sensing device;
   a control circuit configured to determine a position adjustment value based on of the first displacement value and the second displacement value; and
   an actuator configured to modify a position of the ultrasonic transducer based, at least in part, on the position adjustment value.

2. The device of claim 1, wherein the centering device comprises a first surface following guide, a second surface following guide, and a coupling housing coupled to the first surface following guide and the second surface following guide, the coupling housing being biased by a first tension device.

3. The device of claim 2, wherein the plurality of sensors comprises a first sensor and a second sensor.

4. The device of claim 3, wherein the first sensor is coupled to the centering device, and wherein the second sensor is coupled to the surface sensing device.

5. The device of claim 4, wherein the first sensor and the second sensor comprise differential variable reluctance transformers, and wherein the control circuit comprises a processor and a non-volatile memory.

6. The device of claim 1, wherein the first displacement value and second displacement value identify a change in the angle associated with the manufacturing component or a change in a position of the ultrasonic probe assembly relative to the manufacturing component resulting from a modification of the position of the ultrasonic probe assembly.

7. The device of claim 6, wherein the position adjustment value identifies a positional adjustment configured to modify a position of the ultrasonic transducer to offset the change.

8. The device of claim 7, wherein the actuator is configured to modify the position of the ultrasonic transducer to offset the change.

9. The device of claim 1, wherein the ultrasonic transducer is configured to measure one or more structural properties of the manufacturing component.

10. The device of claim 1, wherein the surface sensing device comprises a wheel biased by a second tension device.

11. A method comprising:
    positioning, using a centering device, an ultrasonic probe assembly relative to a manufacturing component to bisect an angle associated with the manufacturing component the ultrasonic probe assembly comprising an ultrasonic transducer;
    identifying a change associated with the position of the ultrasonic probe assembly relative to the manufacturing component, the change being identified based, at least in part, on a previous position of the ultrasonic probe assembly;
    determining, using a control circuit, a position adjustment value based on the identified change; and
    modifying a position of the ultrasonic transducer based, at least in part, on the position adjustment value.

12. The method of claim 11, wherein identifying the change comprises:
    identifying, using a first sensor associated with the centering device, a first displacement value.

13. The method of claim 11, wherein identifying the change comprises:
    identifying, using a second sensor associated with a surface sensing device, a second displacement value.

14. The method of claim 13, wherein the surface sensing device comprises a wheel biased by a tension device.

15. The method of claim 11, wherein the modifying of the position of the ultrasonic transducer is based, at least in part, on the position adjustment value, and offsets the identified change.

16. A system comprising:
    a robotic arm;
    an ultrasonic probe assembly coupled to the robotic arm, the ultrasonic probe assembly comprising:
       a centering device configured to modify a position of the ultrasonic probe assembly relative to a manufacturing component to bisect an angle associated with the manufacturing component;
       a surface sensing device configured to sense a curvature associated with the manufacturing component;
       a plurality of sensors configured to measure a first displacement value associated with the centering device and a second displacement value associated with the surface sensing device;
       an ultrasonic transducer;
       an actuator configured to modify a position of the ultrasonic transducer; and
       an electronics housing comprising a control circuit configured to determine a position adjustment value based on the first displacement value and the second displacement value.

17. The system of claim 16, wherein the centering device comprises a first surface following guide, a second surface following guide, and a coupling device coupled to the first surface following guide and the second surface following guide, the coupling device being biased by a first tension device.

18. The system of claim 16, wherein the first displacement value and second displacement value identify a change in the angle associated with the manufacturing component or a change in a position of the ultrasonic probe assembly relative to the manufacturing component resulting from a modification of the position of the ultrasonic probe assembly.

19. The system of claim 18, wherein the position adjustment value identifies a positional adjustment configured to modify a position of the ultrasonic transducer to offset the change.

20. The system of claim 19, wherein the actuator is configured to modify the position of the ultrasonic transducer based, at least in part, on the position adjustment value to offset the change.

* * * * *